United States Patent
Carvalhães Lago et al.

(10) Patent No.: US 11,071,708 B2
(45) Date of Patent: Jul. 27, 2021

(54) PLANT LIPID COMPOSITION FOR PROMOTING HAIR GROWTH, METHOD FOR PROMOTING HAIR GROWTH AND USE OF SAID PLANT LIPIDS

(71) Applicant: NATURA COSMÉTICOS S.A., São Paulo (BR)

(72) Inventors: Juliana Carvalhães Lago, São Paulo (BR); Daniela Zimbardi, São Paulo (BR); Carla Maria Sanches Scanavez De Paula, São Paulo (BR); Ana Paula Pedroso De Oliveira, São Paulo (BR); Cintia Rosa Ferrari, São Paulo (BR); Caroline Ziegler Stüker, São Paulo (BR); Juliana Beltrame Reigada, São Paulo (BR); Debora Cristina Castellani, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 0 days.

(21) Appl. No.: 16/066,951

(22) PCT Filed: Dec. 27, 2016

(86) PCT No.: PCT/BR2016/050350
§ 371 (c)(1),
(2) Date: Jun. 28, 2018

(87) PCT Pub. No.: WO2017/112990
PCT Pub. Date: Jul. 6, 2017

(65) Prior Publication Data
US 2019/0000748 A1 Jan. 3, 2019

Related U.S. Application Data

(60) Provisional application No. 62/271,413, filed on Dec. 28, 2015.

(51) Int. Cl.
| | |
|---|---|
| A61Q 5/00 | (2006.01) |
| A61K 36/00 | (2006.01) |
| A61K 8/92 | (2006.01) |
| A61Q 7/00 | (2006.01) |
| A61P 17/14 | (2006.01) |
| A61K 36/889 | (2006.01) |

(52) U.S. Cl.
CPC ............ *A61K 8/922* (2013.01); *A61K 36/889* (2013.01); *A61P 17/14* (2018.01); *A61Q 7/00* (2013.01); *A61K 2800/91* (2013.01); *A61K 2800/92* (2013.01)

(58) Field of Classification Search
None
See application file for complete search history.

(56) References Cited

U.S. PATENT DOCUMENTS

| 5,741,496 A | 4/1998 | Khaiat | |
|---|---|---|---|
| 8,906,397 B2 * | 12/2014 | Banov | A61K 31/192 424/401 |
| 2013/0323333 A1 * | 12/2013 | Darsale | A61Q 5/00 424/736 |
| 2014/0065153 A1 | 3/2014 | Christiano et al. | |

FOREIGN PATENT DOCUMENTS

| CA | 2886795 A1 * | 4/2014 | ............ A61Q 17/00 |
|---|---|---|---|
| WO | WO 2014/013014 A1 | 1/2014 | |
| WO | WO 2014/053038 A2 | 4/2014 | |

OTHER PUBLICATIONS

International Search Report and Written Opinion for Application No. PCT/BR2016/050350 dated Mar. 6, 2017, 8 pages.
Extended European Search Report and Application No. EP 16880204.9 dated Jun. 26, 2019, 13 pages.
Aaronson, D. et al. *A Road Map for Those Who Don't Know JAK-STAT*, Science 296 (May 31, 2002) 1653-1655.
Akria, et al., *Molecular Cloning of APRF, a Novel IFN-Stimulated Gene Factor 3 p91-Related Transcription Factor Involved in the gp130-medi8ated Signaling Pathway*, Cell 77 (Apr. 1994) 63-71.
Berg, T., *Inhibition of Transcription Factors With Small Organic Molecules*, Curr Opin Chem Biol. 12 (Aug. 2008) 464-471.
Bowman, T. et al., *STATs in Oncogensis*, Oncogene 19 (2000) 2474-2488.
Bradford, M.M., *A Rapid and Sensititve Method for the Quantitation of Microgram Quantities of Protein Utilizing the Principle of Protein-Dye Binding*, Anal Biochem 72 (1976) 248-254.
Deug, J. et al., *Small Molecule Inhibitors of Stat3 Signaling Pathway*, Curr Cancer Drug Targets, 7 (Feb. 2007) 91-107.
Eeker, A. et al., *The Dark and the Bright Side of Stat3; Proto-Oncogene and Tumor-Suppressor*, Front Biosci. 14 (Jan. 1, 2009) 2944-2958.
Fletcher, S. et al., *Molecular Disruption of Oncogenic Signal Transducer and Activator of Transcription 3 (STAT3) Protein*, Biochem Cell Biol. 87 (2009) 825-833.
Harel, S. et al., *Pharmacologic Inhibition of JAK-STAT Signaling Promotes Hair Growth*, Sci. Adv. (Oct. 23, 2015) 12 pages,
*Guidance Document on Using Cytotoxicity Tests to Estimate Starting Doses for Acute Oral Systemic Toxicity Tests*, No. 129, OECD (Organisation for Economic Co-Operation and Development), OECD Environment, Health and Safety Publications Series on Testing and Assessment, Paris (2010) 54 pages.

(Continued)

Primary Examiner — Susan T Tran
(74) Attorney, Agent, or Firm — Alston & Bird LLP

(57) ABSTRACT

The present invention is directed to cosmetic and/or pharmaceutical compositions comprising at least one plant lipid, preferably pataua (*Oenocarpus bataua*) oil, having as main application promoting hair growth by modulating the expression of genes involved in the JAK-STAT signalling pathway. The present invention also relates to methods for promoting hair growth by modulating the expression of genes involved in the JAK-STAT signalling pathway and to the use of said plant lipids in the preparation of said compositions.

3 Claims, 2 Drawing Sheets

(56) References Cited

OTHER PUBLICATIONS

Rainforest Grown Shampoo, Mintel, Aug. 19, 2010, 4 pages.
Elixir, Aug. 24, 2010, 5 pages.
Rainforest Grown Shampoo, Mintel, Oct. 21, 2011, 5 pages.
Patawa & Moringa Pre and Post Shampoo Hair Oil, Mintel, Aug. 21, 2015, 3 pages.
Alvarez, A. M. R. et al., *Lipids in Pharmaceutical and Cosmetic Preparations*, Grasas y Aceites, vol. 51, Fasc. 1-2 (2000) 74-96.
Levden, J. J. et al., (editors), Skin Moisturization, Cosmetic Science and Technology Series, vol. 25 (2002) 699 pages.

\* cited by examiner

PLANT LIPID COMPOSITION FOR PROMOTING HAIR GROWTH, METHOD FOR PROMOTING HAIR GROWTH AND USE OF SAID PLANT LIPIDS

FIELD OF THE INVENTION

The present invention is directed to cosmetic and/or pharmaceutical compositions comprising at least one plant lipid, preferably pataua (*Oenocarpus bataua*) oil, having as main application promoting hair growth by modulating the expression of genes involved in the JAK-STAT signalling pathway, preferably STAT3. The present invention also relates to methods for promoting hair growth by modulating the expression of genes involved in the JAK-STAT signalling pathway, preferably STAT3, and to the use of said plant lipids in the preparation of said compositions.

BACKGROUND OF THE INVENTION

Lipids are a group consisting of several organic compounds found in animals, plants and microorganisms that possess important energetic and metabolic functions in the organism. Due to the diversity of these compounds, lipids have broad applications in nutrition and in developing cosmetics and pharmaceuticals, and they can also be used in consumer goods industries (paints, detergents, etc.).

Triglycerides, also known as esters of trihydroxy alcohols with three fatty acid molecules attached, are the major lipids found in vegetable oils and butters, which are widely used raw materials. Vegetable oils and butters are water-insoluble substances whose compositions and proportions of triglycerides and fatty acids vary with the species of origin of the material. The main difference between vegetable oils and butters is given by their state at room temperature: oils are liquid and butters are solid. These characteristics are strongly related to the composition of fatty acids in their triglyceride molecules (Alvarez and Rodriguez, 2000).

Plant lipids, such as oils and butters are commonly used in cosmetic and pharmaceutical formulations as emollients, which are agents that moisturize the skin by promoting a reduction of transepidermal water loss (TEWL) (Leyden and Rawlings, 2002). However, there are very few scientific studies that show a biological effect promoted by vegetable oils and butters when inserted into topical compositions.

The Applicant, through extensive scientific research, has found that plant lipids, especially pataua (*Oenocarpus bataua*) oil, modulates the expression of genes of the JAK-STAT signalling pathway, preferably STAT3, which is related to the promotion of hair growth.

Accordingly, the regulation of the expression of these genes via application of plant lipids, preferably pataua (*Oenocarpus bataua*) oil, or cosmetic compositions comprising said lipids represents a particularly novel technological approach for the promotion of hair growth.

BRIEF DESCRIPTION OF THE INVENTION

The object of the present invention is a cosmetic composition, particularly for topical application, which comprises at least one plant lipid, preferably pataua (*Oenocarpus bataua*) oil, and one cosmetically acceptable carrier.

The present invention is also directed to a pharmaceutical composition, particularly for topical application, which comprises at least one plant lipid, preferably pataua (*Oenocarpus bataua*) oil, and one pharmaceutically acceptable carrier.

The present invention further relates to the use of a plant lipid, preferably pataua (*Oenocarpus bataua*) oil, for the preparation of a cosmetic composition for promoting hair growth through the modulation of the expression of genes of the JAK-STAT signalling pathway, preferably through the reduction in the expression of STAT3.

In addition, the present invention is directed to the use of a plant lipid, preferably pataua (*Oenocarpus bataua*) oil, for promoting hair growth through the modulation of the expression of genes of the JAK-STAT signalling pathway, preferably through the reduction in the expression of STAT3.

The present invention also relates to a method of cosmetic or therapeutic treatment comprising applying a plant lipid, preferably pataua (*Oenocarpus bataua*) oil, or the compositions of the present invention to the areas wherein hair growth is desired.

DETAILED DESCRIPTION OF THE INVENTION

Figure 1:
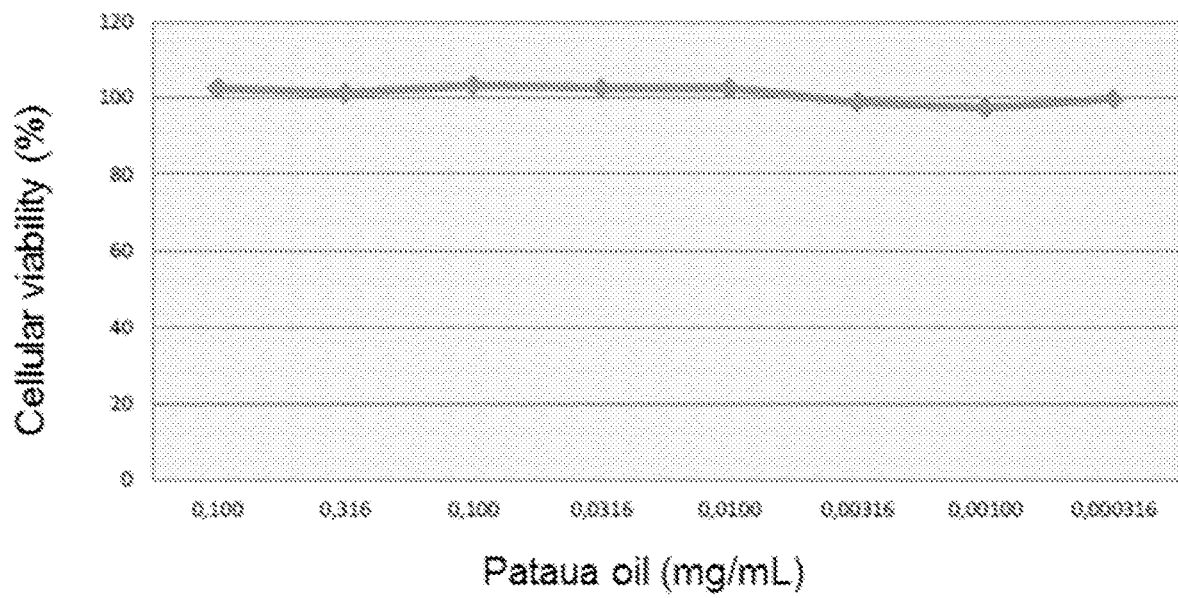
FIG. 1. Assessment of the non-cytotoxic concentrations pataua oil in cultured human keratinocytes after 72 hours of incubation by XTT method.

The present invention relates to cosmetic and/or pharmaceutical compositions, particularly for topical application directed to the promotion of hair growth through the modulation of the expression of genes of the JAK-STAT signalling pathway, preferably STAT3, comprising at least one plant lipid, preferably pataua (*Oenocarpus bataua*) oil, and one cosmetically or pharmaceutically acceptable carrier.

The compositions of the present invention may comprise plant lipids selected from vegetable oils and butters obtained, for example, from plants of the genus *Theobroma, Carapa, Euterpe, Mauritia, Passiflora, Astrocaryum, Oenocarpus, Elaeis* and *Virola*. More preferably, said plant lipids may be selected from acai oil, andiroba oil, buriti oil, passion fruit oil, palm olein, cupuacu butter, cocoa butter, murumuru butter, pataua oil, ucuuba butter and/or a mixture thereof. Most preferably, the compositions of the present invention comprise pataua (*Oenocarpus bataua*) oil.

The amount of plant lipids in the compositions of the present invention naturally depends on the desired cosmetic or pharmaceutical effect and thus may vary widely.

In a particular embodiment, the at least one plant lipid is present in the cosmetic composition of the present invention in an amount ranging from about 0.01% to about 50% by weight, preferably from about 0.5% to about 20 wt %, more preferably about 1% to about 5% by weight, the amounts based on the total weight of the composition.

Compositions

The compositions of the present invention may be ingested, injected or applied directly to the keratinous materials. Depending on the route of administration, the compositions of the present invention may be provided in the galenic and cosmetic forms normally used.

For topical application to the keratinous materials, the compositions of the present invention may be in the form of aqueous, alcoholic or oily solutions, dispersions, emulsions, suspensions, aerosol compositions comprising pressurized propellant agent, microcapsules, microparticles or ionic or non-ionic type vesicular dispersions.

More specifically, by way of example and without limitation, one can mention gels, lotions in general, such as aftershave and fasteners, foams, creams, such as lotions for cleansing, protection, treatment or care of the face, hair (e.g. anti-aging cream and combing cream) or other body regions, makeup removers, such as foundations, lipsticks, face masks, nail polishes, eyeliners, shadows, powders, among other forms known by skilled artisans, sunscreens, milks, mists, oils, butters, bar soaps, liquid rinse soaps or non-rinse soaps, shampoos, conditioners, styling products, restructurers, moisturizers, deodorants, sunscreens, depilatory creams, bath water, makeup, aerosol composition comprising pressurized propellant agent, dye compositions, compositions for permanent waving or straightening and compositions for scalp treatment.

For injectable application, the compositions of the present invention may be provided in the form of an aqueous or oily lotion or in the form of serum.

For oral application, said compositions may be provided in the form of capsules, tablets, granules, syrups, or any other pharmaceutical form known to those skilled in the art.

The quantities of the various constituents of the compositions of the present invention are those conventionally used in the fields considered and are not limitative of the present invention.

The compositions of the present invention are prepared in ways known to those skilled in the art.

Optional Components

To provide the cosmetic composition and the pharmaceutical composition of the present invention with some desirable characteristic not yet achieved with the aforementioned components, optional components may be added which are compatible with the properties thereof. Some of the components that may be added to said compositions are listed below.

A chelating agent may be added to the compositions of the present invention, for example, amino acids, EDTA, dimercaprol and etidronic acid. Said chelating agents may be added at a concentration range between 0.10 and 0.50% of the composition.

The following examples of emulsifiers can be mentioned: alkoxylated carboxylic acids, phosphorus compounds, fatty acids, such as, without limitation, a mixture of glyceryl stearate/PEG-100 stearate, potassium cetyl phosphate, glycerol stearate and polysorbates, for example, polysorbate 60. Said emulsifiers may be present at a concentration of between 1 and 5%.

As examples of moisturizers, biological polymers and derivatives, and also alcohols, such as glycerin and propylene glycol may be mentioned. Said moisturizers may be present at a concentration of between 1 and 10%.

As sunscreens, physical or chemical filters may be added. Examples of sunscreens that may be used in the composition of the present invention are ethylhexyl salicylate, ethylhexyl methoxycinnamate, methyl 4-methoxycinnamate, ethyl 4-methoxycinnamate, octyl 4-methoxycinnamate, octocrylene, benzophenone-3, diethylamino hydroxybenzoyl hexyl benzoate, avobenzone, phenylbenzimidazole sulfonic acid, dietilhexilbutamido triazone, diethanolamide methoxycinnamate, homosalate, ethylhexyl triazone, polysilicon-15, benzoxazoylphenyl ethylhexylamine bis-triazine, 2,6-diethylhexyl naphthalate, butyl methoxydibenzoylmethane, mixture of titanium dioxide, silica and dimethicone (Parsol TX), bisoctrizol (Tinosorb M), bemotrizinol (Tinosorb S), disodium phenyl dibenzimidazol tetrasulphonate (Neo Heliopan AP) or a mixture of one or more thereof. Said filters may be present in the compositions of the present invention at a concentration of between 5 and 40%.

As examples of emollients, esters, fatty acids, alcohols, plant polymers, ethers, oils and fats, such as alkyl benzoate, cetyl lactate, cetiol sensoft, dicaprilyl carbonate, isononyl isononanoate, macadamiate acetate, caprylic/capric triglyceride, pentanediol, palm olein, hexylene glycol may be mentioned. Said emollients may be present at a concentration comprised between 1 and 10%.

As consistency agents, fatty alcohols, for example, cetyl alcohol and cetostearyl alcohol may be mentioned. Said consistency agents may be present at a concentration comprised between 0.2 and 5%.

As thickeners/viscosity agents, carbomers, polymers, gums and salts, for example, alkyl acrylate, Carbopol, xanthan gum and sodium chloride may be added. Said thickeners may be present at a concentration comprised between 0.2 and 5%.

As sensory modifiers, silicones, starches, synthetic polymers and minerals may be added. Examples of sensory modifiers are D5/D6 cyclomethicone, cyclomethicone and dimethicone crospolymer, tapioca starch, nylon, silica, among others. Said modifiers are present in the compositions of the present invention at a concentration of between 1 and 8%.

As an antioxidant, for example, phenols such as BHT, BHA, vitamin C, OPC from grape seeds, or even an antioxidant complex may be added.

In a particular embodiment, an antioxidant complex developed by the applicant, consisting of the combination of coffee extract, lycopene and vitamin E is added.

In another particular embodiment, the antioxidant complex developed by the applicant, consisting of the combination of green tea extract, dry cocoa extract and tocopheryl acetate is added.

Said antioxidant may be present at a concentration between 0.1 and 0.5% of the composition.

As oils and waxes that can be used in the composition of the present invention vaseline, shea butter, sunflower oil, perhydrosqualene, purcelin oil, silicone oil, cyclomethicone, beeswax, carnauba wax, paraffin, among others.

As an example of solvents water, oils or lower alcohols, especially ethanol and isopropanol and propylene glycol.

As gelling agents, hydrophilic gelling agents may be added, such as carboxyvinyl polymers (carbomer), acrylic copolymers, such as acrylate/alkyl acrylate copolymers, polyacrylamides, polysaccharides, such as hydroxypropylcellulose, naturally-occurring gums and clays. As lipophilic gelling agents, bentones, metal salts of fatty acids may be mentioned, such as aluminum stearates and hydrophobic silica, ethylcellulose and polyethylene.

As preservative agent, alcohols and heterocyclic compounds may be added, such as phenoxyethanol, methylchloroisothiazolinone and methylisothiazolinone. Said preservative agent may be present in the compositions of the present invention at a concentration comprised between 0.01 and 2%.

As pH correction agents, alkanolamines and inorganic bases may be added, such as triethanolamine, sodium hydroxide, and others known to the person skilled in the art. Said correction agents are added in an amount sufficient to achieve the desired pH.

Conditioning agents may also be added, such as dimethicone, dimethiconol TEA or a combination of dimethiconol and TEA dodecylbenzenesulphonate.

Conventional surfactants may also be added, such as cocoamido propyl betaine, decyl polyglucose and sodium lauryl ether sulfate.

Pearlizing agents may also be added, such as glycol distearate, ethylene glycol distearate or diethylene glycol distearate.

Optional Additional Actives

If desired, additional actives may be added to the cosmetic and/or pharmaceutical compositions of the present invention. Among them, the following actives may be mentioned, for example:

proteins and protein hydrolysates, amino acids, urea, allantoin, sugars and sugar derivatives, such as biosaccharide gum, particularly biosaccharide gum 3, vitamins such as retinol (vitamin A), tocopherol (vitamin E) and derivatives thereof, alcohols and plant extracts, such as, without limitation, *Passiflora alata* extract, green tea, grape OPC, cocoa extract, jambu extract, essential oil of pitanga, among others, essential fatty acids, ceramides, essential oils, salicylic acid and derivatives thereof;

modulating agents of skin pigmentation and/or proliferation and/or differentiation, such as retinoic acid and its isomers, retinol and its esters, vitamin D and its derivatives, estrogens, such as estradiol, levonorgestrel, ethinyl estradiol, kojic acid and hydroquinone;

antibacterial agents, such as clindamycin phosphate, erythromycin, or antibiotics of the tetracycline class;

antiparasitic agents, in particular metronidazole, crotamiton or pyrethroids;

antifungal agents, especially compounds of the imidazole class, such as econazole, ketoconazole or miconazole and salts thereof, polyene compounds, such as amphotericin B, compounds of the allylamine family, such as terbinafine, or alternatively octopirox;

antiviral agents, such as acyclovir;

steroidal anti-inflammatory agents, such as hydrocortisone, betamethasone valerate, clobetasol propionate or non-steroidal anti-inflammatory agents, such as ibuprofen and salts thereof, celecoxib and salts thereof, diclofenac and salts thereof, acetylsalicylic acid, acetaminophen or glycyrrhetinic acid;

anesthetic agents, such as lidocaine hydrochloride and derivatives thereof;

antipruritic agents, such as thenaldine, trimeprazine or cycloheptadine;

keratolytic agents, such as alpha- and beta-hydroxycarboxylic acids or beta-keto carboxylic acids, their salts, amides or esters, glycolic acid, lactic acid, salicylic acid, citric acid, n-octanol-5-salicylic acid, among others.

anti-free radical agents, such as alpha-tocopherol and esters thereof, superoxide dismutases, metallic chelating agents or ascorbic acid and esters thereof;

antiseborrheic agents, such as progesterone;

antidandruff agents, such as zinc pyrithione and octopirox;

antiacne agents, such as retinoic acid and benzoyl peroxide;

anti hair loss agents, such as minoxidil;

antilipemic agents, such as atorvastatin, simvastatin, pravastatin;

antidrepressive agents/muscle relaxant agents, such as, without limitation, venlafaxine, lorazepam, gabapentin;

anti-acid secretion agents, such as omeprazole, lansoprazole, dexlansoprazole, esomeprazole, pantoprazole, rabeprazole;

diuretic agents, such as hydrochlorothiazide, sildenafil citrate.

Method

The present invention also relates to a method of promoting hair growth comprising applying the effective amount of the plant lipid, preferably pataua (*Oenocarpus bataua*) oil, or composition of the present invention in the region wherein hair growth is desired.

In a preferred embodiment, the method of promoting hair growth of the present invention comprises modulating the expression of genes of the JAK-STAT signalling pathway, preferably through the reduction in the expression of STAT3, by administering a plant lipid or composition as defined in the present invention.

The person skilled in the art will know how to choose the optimum composition for the desired end in the teachings disclosed in the present specification.

Use

The present invention further relates to the use of a plant lipid, preferably pataua (*Oenocarpus bataua*) oil, for the preparation of a cosmetic or pharmaceutical composition for promoting hair growth through the modulation of the expression of genes of the JAK-STAT signalling pathway, preferably through the reduction in the expression of STAT3.

Genes Modulated by the Compositions of the Present Invention

The compositions of the present invention have attributes of interest for the promotion of hair growth by modulating the expression of genes of the JAK-STAT signalling pathway, preferably through the reduction in the expression of STAT3, as can be seen below in the examples presented.

JAK-STAT Signalling Pathway

The JAK-STAT signalling pathway transmits information from chemical signals outside the cell, through the cell membrane, and into gene promoters on the DNA in the cell nucleus, which causes DNA transcription and activity in the cell. The JAK-STAT system is a major signalling alternative to the second messenger system.

The JAK-STAT system consists of three main components: (1) a receptor (2) Janus kinase (JAK) and (3) Signal Transducer and Activator of Transcription (STAT) (Aaronson and Horvath, 2002).

Many JAK-STAT pathways are expressed in white blood cells, and are therefore involved in regulation of the immune system.

The receptor is activated by a signal from interferon, interleukin, growth factors, or other chemical messengers. This activates the kinase function of JAK, which autophosphorylates itself (phosphate groups act as "on" and "off" switches on proteins). The STAT protein then binds to the phosphorylated receptor, where STAT is phosphorylated by JAK. The phosphorylated STAT protein binds to another phosphorylated STAT protein (dimerizes) and translocates into the cell nucleus. In the nucleus, it binds to DNA and promotes transcription of genes responsive to STAT.

In mammals, there are seven STAT genes, and each one binds to a different DNA sequence. STAT binds to a DNA sequence called a promoter, which controls the expression of other DNA sequences. This affects basic cell functions, like cell growth, differentiation and death. (Aaronson and Horvath, 2002)

The JAK-STAT pathway is evolutionarily conserved, from slime molds and worms to mammals (but not fungi or plants). Disrupted or deregulated JAK-STAT functionality (which is usually by inherited or acquired genetic defects) can result in immune deficiency syndromes and cancers (Aaronson and Horvath, 2002).

STAT Gene/Proteins proteins of the STAT (signal transducer and activator of transcription) family, are phosphorylated in response to cytokines and growth factors, by kinases associated with the receptor and then form homo or heterodimers that translocate to the cell nucleus where they act as transcription factors. Specifically, these proteins are activated by phosphorylation of tyrosine 705 in response to interferons, epidermal growth factor (EGF), the interleukins (IL-5, IL-6 and IL-10), hepatocyte growth factor (HGF), the leukemia inhibitory factor (LIF), bone morphogenetic protein 2 (BMP-2) and also to the hormone leptin. STAT3 can highlighted within the STAT family, as it mediates expression of a variety of genes in response to biological stimuli, such as cell growth and apoptosis (Akira et al, 1994).

Several studies describe the synthesis of inhibitory molecules acting on signalling pathways mediated by this protein, probably due to the oncogenic potential of STAT3 (Bowman et al, 2000; Ecker et al, 2009). Among the existing approaches are: i) antagonists of receptors which activate STAT3; ii) molecules that directly affect the STAT3 activity as inhibitory peptide sequences, peptide-mimetics, small inhibitory molecules and inhibitors containing platinum atoms; iii) double-stranded sequences of DNA (oligonucleotide decoy or ODN), similar to those found in promoter regions of target genes of STAT3 (Fletcher et al, 2008).

Given the difficulty to synthesize functional chemical structures that carry out this role inhibitor, several research centres seek to block STAT3 using small molecules (Deng et al, 2007; Fletcher et al, 2008; Berg et al, 2008), identified through testing cytotoxicity from chemical libraries, such as plant extracts or synthetic molecules rationally generated by computer analysis.

EXAMPLES

Example 1—Gene Expression Modulation

The expression of genes was tested in a reconstructed human epidermis culture (EPI/001, StratiCELL®) samples treated with 1% pataua (*Oenocarpus bataua*) oil diluted in mineral oil. Control samples were treated with only mineral oil. Each treatment was reproduced in three different samples for a period of 6 hours. After this period, the tissues were bathed in lysis buffer, after which the RNA was extracted with a Qiagen RNAeasy kit. The amount and quality of the RNA was evaluated by a Ultraspec 1100 Pro (Amersham) spectrophotometer and a Agilent Bioanalyzer 2100—Agilent RNA 6000 Nano Kit, respectively. The reverse transcription was performed with a High-Capacity RNA-to-cDNA kit (Applied Biosystems).

The synthetized cDNA was assayed in custom qPCR arrays comprising 379 genes in the 7900HT Fast Real-Time System (Applied Biosystems) equipment. The Ct (threshold cycles) values were calculated for each gene/condition/sample and the relative quantification was performed according to the ΔΔCt method. This method compares the Ct values obtained for the treated conditions with the control condition (without treatment or control treatment). In the present study, the control refers to samples treated only with mineral oil, which is the solvent used for the solubilisation of the plant lipids of the present invention. The Ct values for both treated and control samples were then normalized with the value for the housekeeping gene, which for the present study is the 18S gene. After said steps, only the relative expression values having a cutoff>2.00 were selected. For statistical analysis, the t test was employed, being considered as statistically significant when P<0.05.

The results are show in Table 1 below.

TABLE 1 genes which had its expression modulated by the treatment with pataua (*Oenocarpus bataua*) oil.

| Gene | RQ | teste.t | |
|---|---|---|---|
| AQP3-Hs00185020_m1 | 0.172683243 | 0.009109257 | ↑ |
| ASAH1-Hs01001661_m1 | 0.205612517 | 0.020464878 | ↑ |
| ATR-Hs00354807_m1 | 0.107186863 | 0.003998860 | ↑ |
| BTC-Hs01101204_m1 | 86.917011570 | 0.013724369 | ↓ |
| CASP1-Hs00354836_m1 | 0.145490817 | 0.009966042 | ↑ |
| CCND1-Hs00765553_m1 | 0.168023314 | 0.032466293 | ↑ |
| CCR10-Hs00706455_s1 | 0.011259865 | 0.038102989 | ↑ |
| CDH1-Hs01023895_m1 | 0.124922045 | 0.017210872 | ↑ |
| CDSN-Hs00381831_m1 | 5.162130690 | 0.000343453 | ↓ |
| CKMT1B; CKMT1A-Hs00179727_m1 | 0.124962460 | 0.006412770 | ↑ |
| CLDN1-Hs01076359_m1 | 0.195557757 | 0.032714770 | ↑ |
| CRABP2-Hs00275636_m1 | 0.191254642 | 0.010738018 | ↑ |
| CREBBP-Hs00231733_m1 | 0.261491025 | 0.019128553 | ↑ |
| CST3-Hs00969174_m1 | 0.280816576 | 0.040292107 | ↑ |
| CST6-Hs00154599_m1 | 3.264963054 | 0.002728700 | ↓ |
| CTSL1-Hs00377632_m1 | 0.252566173 | 0.013441253 | ↑ |
| CTSL2-Hs00952036_m1 | 5.823150880 | 0.002392010 | ↓ |
| DEFB1-Hs00608345_m1 | 0.207727866 | 0.020407860 | ↑ |
| DSC1-Hs00245189_m1 | 0.111418961 | 0.008826597 | ↑ |
| DSG1-Hs00170047_m1 | 0.113453000 | 0.014004671 | ↑ |
| DSG3-Hs00170075_m1 | 0.132592095 | 0.022758096 | ↑ |
| DSP-Hs00189422_m1 | 0.107491911 | 0.005823961 | ↑ |
| EVPL-Hs00157430_m1 | 0.159194971 | 0.002915445 | ↑ |
| G6PD-Hs00166169_m1 | 0.161137777 | 0.005501179 | ↑ |
| GADD45G-Hs00198672_m1 | 0.109552932 | 0.040097146 | ↑ |
| GJA1-Hs00748445_s1 | 0.198948464 | 0.008278856 | ↑ |
| HADHB-Hs00264758_m1 | 0.198700398 | 0.044617474 | ↑ |
| HAS3-Hs00193436_m1 | 2.473636193 | 0.012201328 | ↓ |
| HMGCR-Hs01102995_g1 | 0.194674164 | 0.029854192 | ↑ |
| HMOX1-Hs00157965_m1 | 17.609719210 | 0.000081541 | ↓ |
| HSD17B2-Hs00157993_m1 | 0.314086390 | 0.047214557 | ↑ |
| HSPA1B; HSPA1A-Hs00271244_s1 | 0.092203586 | 0.007614929 | ↑ |
| IL11-Hs00174148_m1 | 3.058731209 | 0.035259235 | ↓ |
| IL1A-Hs00174092_m1 | 0.118191648 | 0.002766680 | ↑ |
| IL1B-Hs00174097_m1 | 0.069933782 | 0.004163750 | ↑ |
| IL1R2-Hs01030384_m1 | 2.266867395 | 0.019843067 | ↓ |
| IL8-Hs01567912_g1 | 0.137967465 | 0.029459776 | ↑ |
| ITGA6-Hs01041011_m1 | 2.493144784 | 0.032747658 | ↓ |
| JUP-Hs00158408_m1 | 0.180891936 | 0.022267126 | ↑ |
| KLK5-Hs00202752_m1 | 3.591118683 | 0.000886089 | ↓ |
| KRT1-Hs00196158_m1 | 0.113219942 | 0.013832352 | ↑ |
| KRT10-Hs00166289_m1 | 0.181293612 | 0.013054507 | ↑ |
| KRT6A-Hs01699178_g1 | 0.262635408 | 0.048329180 | ↑ |
| LAMB1-Hs01055971_m1 | 0.188717485 | 0.036079233 | ↑ |
| LCE2B-Hs00863535_g1 | 673.748649900 | 0.001051567 | ↓ |
| LOR-Hs01894962_s1 | 17.432408450 | 0.005079704 | ↓ |
| MAX-Hs00231142_m1 | 0.224128808 | 0.012042140 | ↑ |
| MDM2-Hs01066930_m1 | 0.257920795 | 0.044537273 | ↑ |
| MMP10-Hs00233987_m1 | 0.004189905 | 0.023997288 | ↑ |
| MMP2-Hs00234422_m1 | 3.335107660 | 0.035431042 | ↓ |
| OGG1-Hs00213454_m1 | 0.123401628 | 0.028254793 | ↑ |
| PCNA-Hs99999177_g1 | 0.204022476 | 0.047841467 | ↑ |
| PCSK6-Hs00159844_m1 | 0.150722496 | 0.028171851 | ↑ |
| PLA2G7-Hs00173726_m1 | 0.222164468 | 0.016201153 | ↑ |
| PLD2-Hs00160163_m1 | 0.168450895 | 0.001302714 | ↑ |
| POLR2A-Hs01108291_m1 | 0.103600294 | 0.008438399 | ↑ |
| PPL-Hs00160312_m1 | 0.206784507 | 0.027315596 | ↑ |
| PRDX6-Hs00705355_s1 | 0.169516781 | 0.008639549 | ↑ |

TABLE 1-continued genes which had its expression modulated by the treatment with pataua (*Oenocarpus bataua*) oil.

| Gene | RQ | teste.t | |
|---|---|---|---|
| PRSS8-Hs00173606_m1 | 2.006340774 | 0.004349869 | ↓ |
| PSAP-Hs01551088_g1 | 0.228099207 | 0.031334279 | ↑ |
| PTGS1-Hs00377726_m1 | 0.136398530 | 0.007262554 | ↑ |
| RNASE7-Hs00922963_s1 | 23.925325820 | 0.001121422 | ↓ |
| RPLP0; RPLP0P6-Hs00420895_gH | 0.098484011 | 0.001254879 | ↑ |
| SERPINE1-Hs01126607_g1 | 4.008882131 | 0.001373450 | ↓ |
| SLPI-Hs00268204_m1 | 0.241807908 | 0.013156857 | ↑ |
| SOD1-Hs00533490_m1 | 0.201613852 | 0.027958305 | ↑ |
| SPRR1B-Hs00234164_m1 | 0.232924344 | 0.015969285 | ↑ |
| SPTLC1-Hs00272311_m1 | 0.242081824 | 0.034467566 | ↑ |
| SPTLC2-Hs00191585_m1 | 0.227388837 | 0.046406824 | ↑ |
| SPTLC3-Hs00217867_m1 | 0.196055407 | 0.038720270 | ↑ |
| SREBF2-Hs01081778_m1 | 0.224974491 | 0.040285446 | ↑ |
| STAT1-Hs01014002_m1 | 0.202734942 | 0.015709720 | ↑ |
| STAT3-Hs00374280_m1 | 0.169924604 | 0.016518387 | ↑ |
| STS-Hs00996676_m1 | 2.308837547 | 0.035170500 | ↓ |
| TERF1-Hs00744634_s1 | 0.136404833 | 0.001327700 | ↑ |
| TERF2-Hs00194619_m1 | 0.157359189 | 0.002520223 | ↑ |
| TGFB1-Hs00998133_m1 | 3.916142692 | 0.012177433 | ↓ |
| TGM3-Hs00162752_m1 | 0.115909174 | 0.019426446 | ↑ |
| TGM5-Hs00909973_m1 | 0.276509317 | 0.043002883 | ↑ |
| TJP1-Hs01551876_m1 | 0.134722869 | 0.027516646 | ↑ |
| TLR5-Hs00152825_m1 | 0.088302617 | 0.012357113 | ↑ |
| TP53-Hs01034254_g1 | 0.253056833 | 0.027928037 | ↑ |
| TRPV4-Hs00222101_m1 | 3.434975955 | 0.020599355 | ↓ |

Results

The expression of 83 genes was modulated by the treatment with pataua oil. Among which, STAT3 which belongs to the JAK-STAT signalling pathway, had its expression significantly reduced.

Example 2—Protein Quantification

1. Cellular Cultures

Human keratinocytes (HaCat—BCRJ Cat 0341) and fibroblasts (HFF-1—BCRJ Cat 0275) were seeded in 75 cm$^2$ bottles (Nunc, Denmark), cultured and expanded in incubator at 37° C. in the presence of 5% CO2, using specific culture medium. Upon reaching confluence, the cells were seeded in 96-well plates (Nunc) for determination of non-cytotoxic concentrations of the test and in 6-well plates (Nunc) for quantification of STAT3.

2. Determination of Non-Cytotoxic Concentrations for Efficacy Trial

The cell viability assay was conducted according to the protocol of OECD No. 129. Pataua oil solubility was tested in culture medium, DMSO and ethanol. Only this latter solvent was able to produce a homogeneous solution. Thus, 100 mg of Pataua oil was solubilized in 1 ml of absolute ethanol (EtOH). Then, there was a dilution of this first solution in culture medium to reach a final concentration of 0.5% EtOH and 0.100 mg Pataua oil.

Cell viability was determined by a colorimetric method using the XTT (2,3-bis[2-methoxy-4-nitro-5-sulfopheny]-2H-tetrazolium-5-carboxyanilide inner salt) dye, which is converted into water-soluble formazan orange by the mitochondrial enzyme succinate dehydrogenase in viable cells (Xenometrix AG, Switzerland). Fibroblasts were seeded at a density of $1 \times 10^4$ cells per well and incubated with test substance in 8 concentrations using a decimal geometric dilution (OECD 129). After 72 hours of incubation the test product was removed and culture medium was replaced. The XTT was then added to the culture and the plate incubated for a further 3 hours. The absorbance (optical density—OD) of each well was determined at 480 nm in the Multiskan GO monochromator (Thermo Fisher Scientific, Vantaa, Finland). The percentage of cell viability was calculated according to the equation: % viability=(DOST/DOCN)×100, where DOST=optical density of the test and DOCN=optical density of the negative control.

3. Incubation of the Cultures with the Test Substance

The cultures of keratinocytes and fibroblasts were incubated with 5 non-cytotoxic concentrations of the test substance determined according to the item 2. The concentrations evaluated in this study to Pataua oil were 0.100; 0.051; 0.0316; 0.0178 and 0.0100 mg/ml (Dilution Factor 1.78) 7. Cells were maintained in contact with the test substance for 72 hours. Cells were then lysed and nuclear protein fraction was extracted using a commercially available extraction kit (Nuclear Extraction Kit—Cayman Chemical Company) for quantification of STAT3.

4. Quantification of STAT3

The quantification of STAT3 was performed by ELISA sandwich assay using a commercially obtained kit (Rheabiotech). The reading of absorbance was performed on monochromator Multiskan GO (Terms Thermo Fisher Scientific, Vantaa, Finland). The STAT3 values were normalized by total protein of the sample measured by Bradford8 technique.

5. Statistical Analysis

For statistical evaluation the ANOVA test that allowed measuring the variation of the results by comparing the data between groups was used. Then the Bonferroni post-test, which strengthened and made even more precise results presented in ANOVA was applied. A significance level of 5% (GraphPad Prism v6) was used.

5.1. Cell Viability

Figure 2:
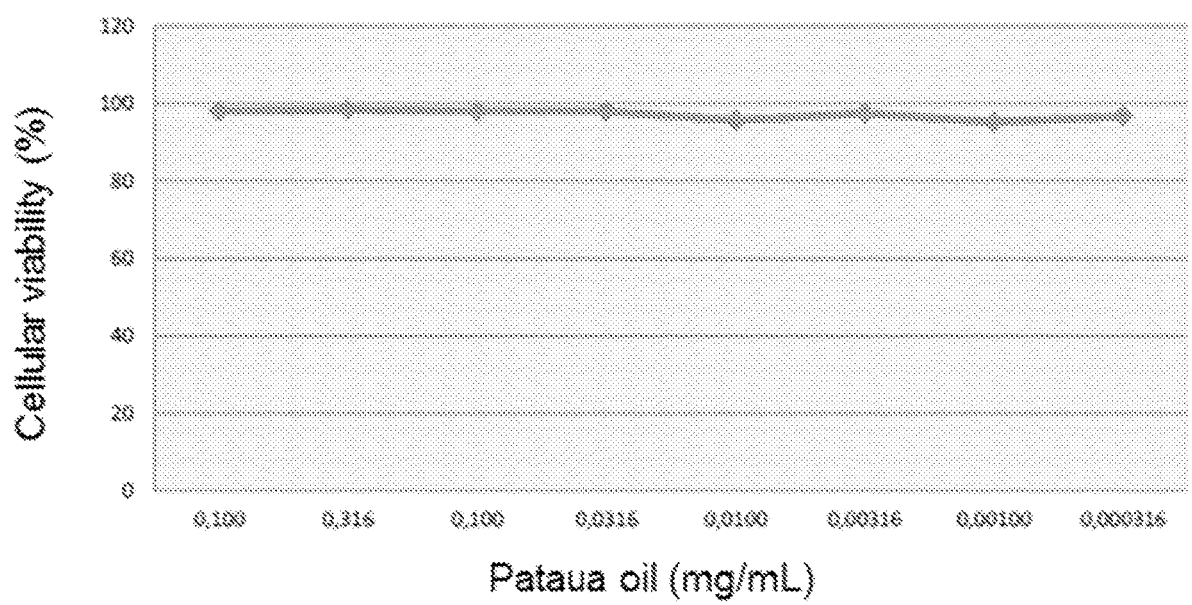
FIG. 2. Evaluation of non-cytotoxic concentrations pataua oil in cultured human fibroblasts after 72 hours of incubation by XTT method.

As can be seen in FIGS. 1 and 2, Pataua oil did not show cytotoxic concentrations neither in cultured keratinocytes or in cultured fibroblasts at the concentrations evaluated.

5.2. STAT3 Synthesis

Figure 3:
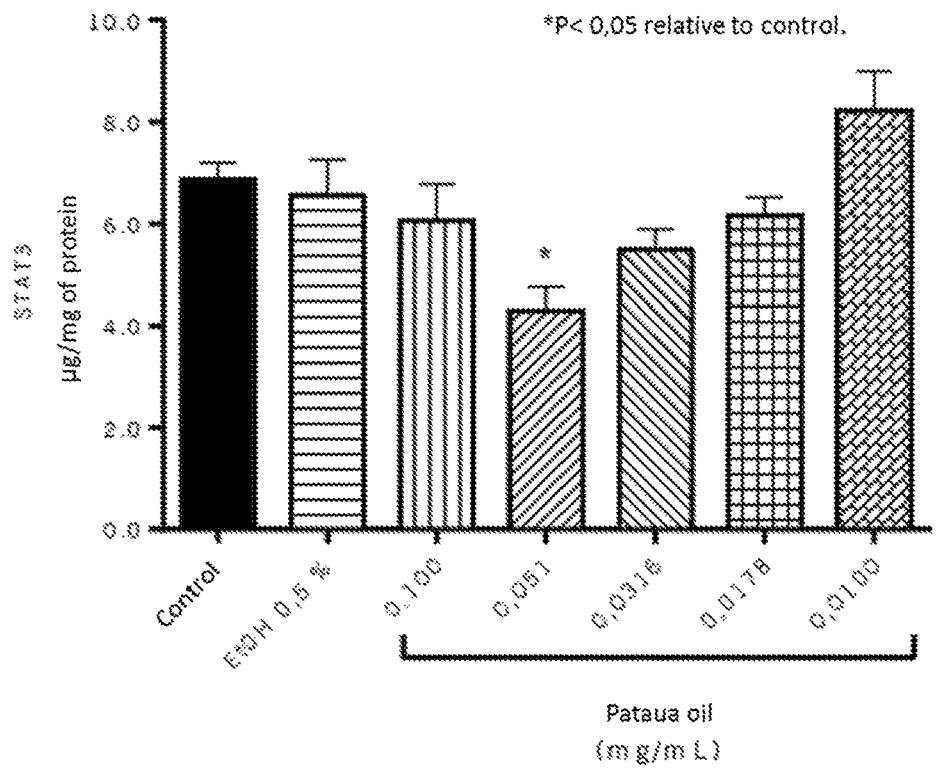
FIG. 3. Effect of pataua oil in STAT3 synthesis in cultured human keratinocytes. The data represent the mean±SD of 3 replicates (ANOVA, Bonferroni).
Figure 4:
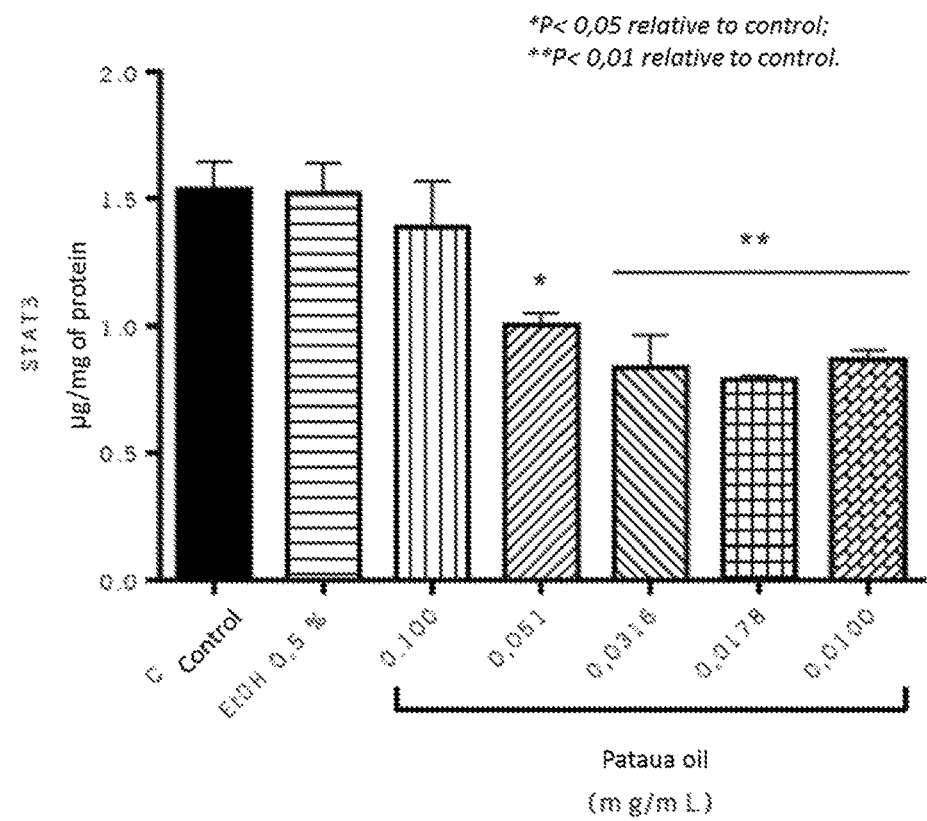
FIG. 4. Effect of pataua oil on STAT3 synthesis in cultured human fibroblasts. The data represent the mean±SD of 3 replicates (ANOVA, Bonferroni).

FIGS. 3 and 4 represent the effects of Pataua oil in STAT3 synthesis in cultures of keratinocytes and human fibroblasts, respectively.

As can be seen, the Pataua oil promoted a statistically significant decrease in the measured protein synthesis in both cell cultures.

Specifically, in cultures of human keratinocytes, Pataua oil significantly inhibited the production of STAT3 in the concentration of 0.051 mg/mL reaching 37.52% reduction, compared to the control group.

Likewise, the Pataua oil inhibited the production of STAT3 protein in cultures of human fibroblasts at concentrations 0.051; 0.0316; 0.0178 and 0.0100 mg/mL decrease reaching up to 48.65% in the control group at 0.0178 mg/ml (P>0.01).

According to the results, it can be concluded that Pataua oil:

showed no cytotoxic concentrations observed in dilutions;

in keratinocyte culture, Pataua oil promotes decrease of 37.52% in the levels of STAT3 in the concentration of 0.051 mg/mL, compared to the control group;

in fibroblast culture, Pataua oil promotes reduction of up to 48.65% in the levels of STAT3 in the concentration of 0.0178 mg/mL, compared to the control group.

Example 3—Shampoo Composition

| Function | Components |
|---|---|
| Surfactants | Cocoamido Propyl Betaine |
| | Decyl Polyglucose |
| | Sodium Lauryl Ether Sulfate |
| Chelating Agent | EDTA |
| Preservative | Kathon |
| Conditioner | Dimethicone, Dimethiconol TEA |
| Viscosity Agent | Carbopol Aqua, Sodium Chloride |
| Perfuming | Fragrances |
| Pearlizing | Glycol distearate |
| pH Correction | Triethanolamine |

Example 4—Body Oil

| Function | Components |
|---|---|
| Emollients | Palm Olein |
| | Hexylene glycol |
| Chelating Agent | EDTA |
| Preservative | Kathon |
| Viscosity Agent | Sodium chloride |
| Perfuming | Fragrances |
| Deodorant Active | Sensiva |

REFERENCES

Aaronson D S, Horvath C M (May 2002). "A road map for those who don't know JAK-STAT". Science 296 (5573): 1653-5.

Akira S, Nishio Y, Inoue M, Wang X J, Wei S, Matsusaka T, Yoshida K, Sudo T, Naruto M, Kishimoto T. Molecular cloning of APRF, a novel IFN-stimulated gene factor 3 p91-related transcription factor involved in the gp130-mediated signaling pathway. Cell 1994 April; 77(1): 63-71.

Berg T. Inhibition of transcription factors with small organic molecules. Curr Opin Chem Biol. 2008 August; 12(4): 464-71.

Bowman T, Garcia R, Turkson J, Jove R. STATs in oncogenesis. Oncogene. 2000 May 15; 19(21):2474-88.

Deng J, Grande F, Neamati N. Small molecule inhibitors of Stat3 signaling pathway. Curr Cancer Drug Targets. 2007 February; 7(1): 91-107.

Ecker A, Simma O, Hoelbl A, Kenner L, Beug H, Moriggl R, Sexl V. The dark and the bright side of Stat3: proto-oncogene and tumor-suppressor. Front Biosci. 2009 Jan. 1; 14:2944-58.

Fletcher S, Drewry J A, Shahani V M, Page B D, Gunning P T. Molecular disruption of oncogenic signal transducer and activator of transcription 3 (STAT3) protein. Biochem Cell Biol. 2009 December; 87(6):825-33.

OECD (Organisation for Economic Co-operation and Development) 129 GUIDANCE DOCUMENT ON USING CYTOTOXICITY TESTS TO ESTIMATE STARTING DOSES FOR ACUTE ORAL SYSTEMIC TOXICITY TESTS. OECD Environment, Health and Safety Publications Series on Testing and Assessment, Paris, 2010.

Bradford, M. M. Rapid and sensitive method for the quantitation of microgram quantities of protein utilizing the principle of protein-dye binding. Anal Biochem 1976; 72: 248-54.

The invention claimed is:

1. A method for promoting hair growth, comprising the step of administering to an individual a composition for promoting hair growth comprising pataua (*Oenocarpus bataua*) oil and a pharmaceutically and/or cosmetically acceptable carrier, wherein the pataua (*Oenocarpus bataua*) oil is present in an amount of about 1% by weight based on the total weight of the composition; and wherein the hair growth is promoted by modulating the expression of genes related to the JAK-STAT signalling pathway.

2. The method according to claim 1, wherein the composition is formulated for topical, oral or parenteral administration.

3. The method according to claim 1, wherein the composition is formulated as aqueous, alcoholic or oily solutions, dispersions, emulsions, suspensions, aerosol compositions comprising a pressurized propellant agent, microcapsules, microparticles or vesicular dispersions of the ionic or non-ionic type, aqueous or oily lotions, serum, capsules, tablets, granules or syrups.

* * * * *